United States Patent [19]

Durham et al.

[11] Patent Number: 5,049,151

[45] Date of Patent: Sep. 17, 1991

[54] MAGNETIC POSITIONER ARRANGEMENT FOR LOCKING SCREWS FOR ORTHOPEDIC HARDWARD

[76] Inventors: Alfred A. Durham, 2954 Lockridge Rd.; Dallas P. Crickenberger, 3465 Westridge Rd., both of Roanoke, Va. 24014

[21] Appl. No.: 453,967

[22] Filed: Dec. 20, 1989

[51] Int. Cl.$^5$ .............................................. A61B 17/56
[52] U.S. Cl. ...................................... 606/98; 606/96
[58] Field of Search ............... 606/96, 97, 98; 33/262, 33/286, 263, 334

[56] References Cited

U.S. PATENT DOCUMENTS

| | | | |
|---|---|---|---|
| 4,621,628 | 11/1986 | Bruderman | 606/97 |
| 4,803,976 | 2/1989 | Frigg et al. | 606/97 |
| 4,850,344 | 7/1989 | Olerud et al. | 606/97 |
| 4,865,025 | 9/1989 | Buzzi et al. | 606/96 |
| 4,877,019 | 10/1989 | Vives | 606/64 |
| 4,881,535 | 11/1989 | Sohngen | 606/98 |
| 4,901,711 | 2/1990 | Goble et al. | 606/97 X |
| 4,917,111 | 4/1990 | Pennig et al. | 606/97 |

FOREIGN PATENT DOCUMENTS

| | | | |
|---|---|---|---|
| 221356 | 4/1985 | German Democratic Rep. | 606/98 |
| 668692 | 1/1989 | Switzerland | 606/96 |

Primary Examiner—Robert A. Hafer
Assistant Examiner—Kevin G. Rooney
Attorney, Agent, or Firm—Larson and Taylor

[57] ABSTRACT

A method and apparatus are provided for rapidly and precisely positioning locking screws or pins into corresponding screw holes in a orthopedic aid such as an intramedullary interlocking rod implanted in a long bone of the limb of a patient, so as to lock the rod in place in the bone. A first magnet is positioned at the location of a screw hole in the rod and an aiming device, comprising a second magnet pivotably mounted so as to be able to be brought in alignment with the first magnet, is used to locate the first magnet and hence enable a screw or pin to be guided into place through the bone into the screw hole in the rod to lock the rod in position. In one embodiment, an elongate insertion member which carries the first magnet at the distal end thereof is used to position the first magnet at the level of the hole in the rod while in a second embodiment, a solid rod is used and the magnet is removably disposed within the hole in the rod prior to implantation of the rod.

25 Claims, 4 Drawing Sheets

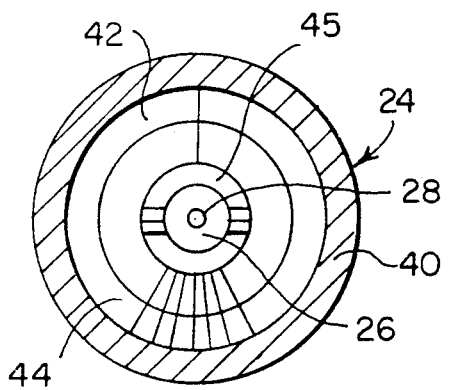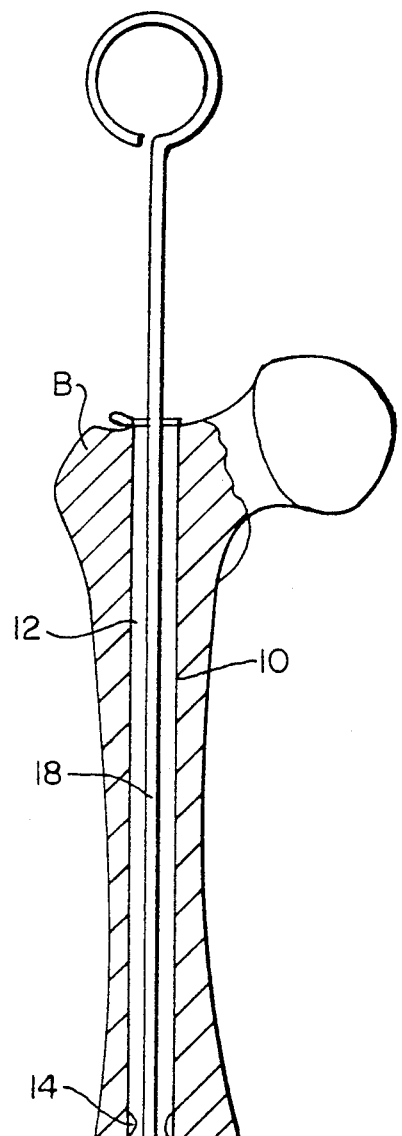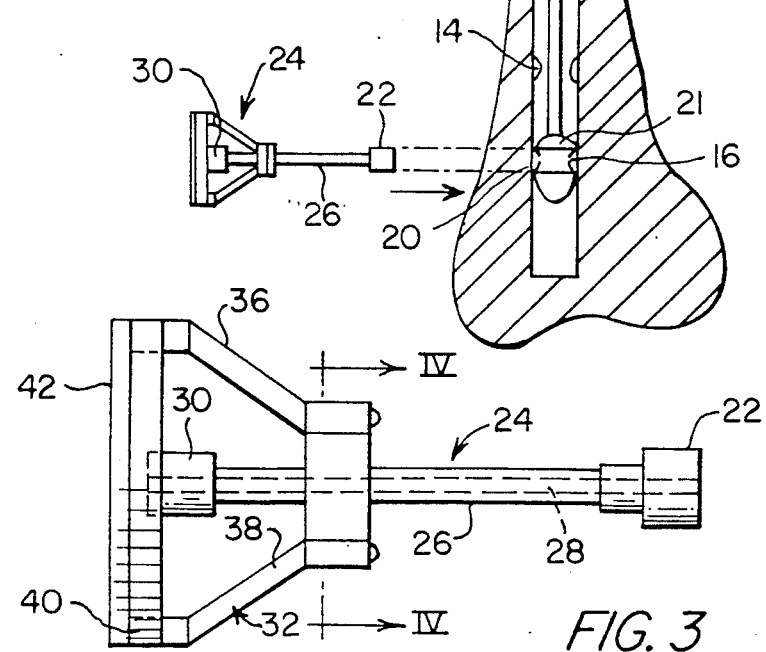

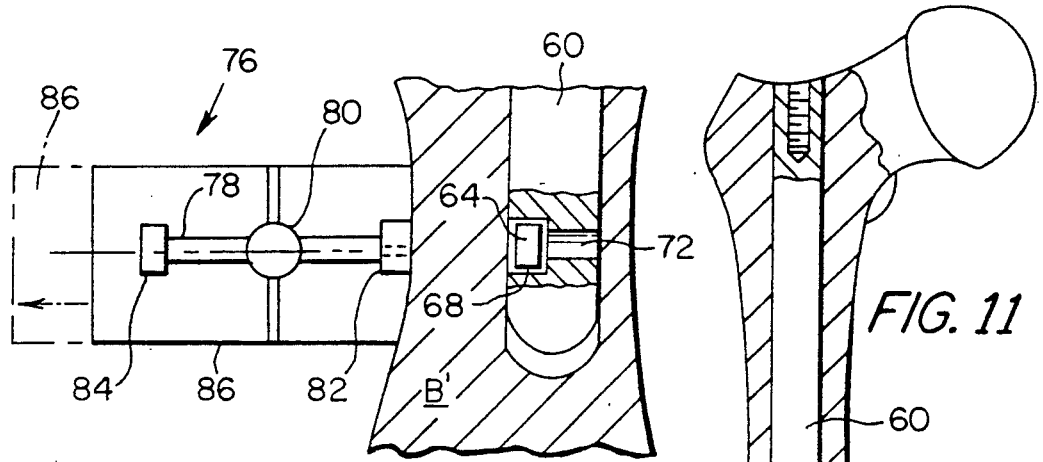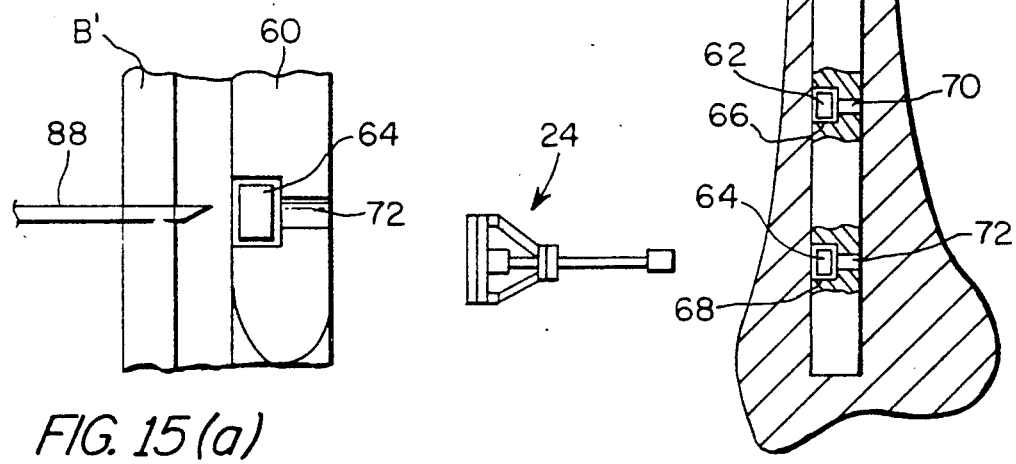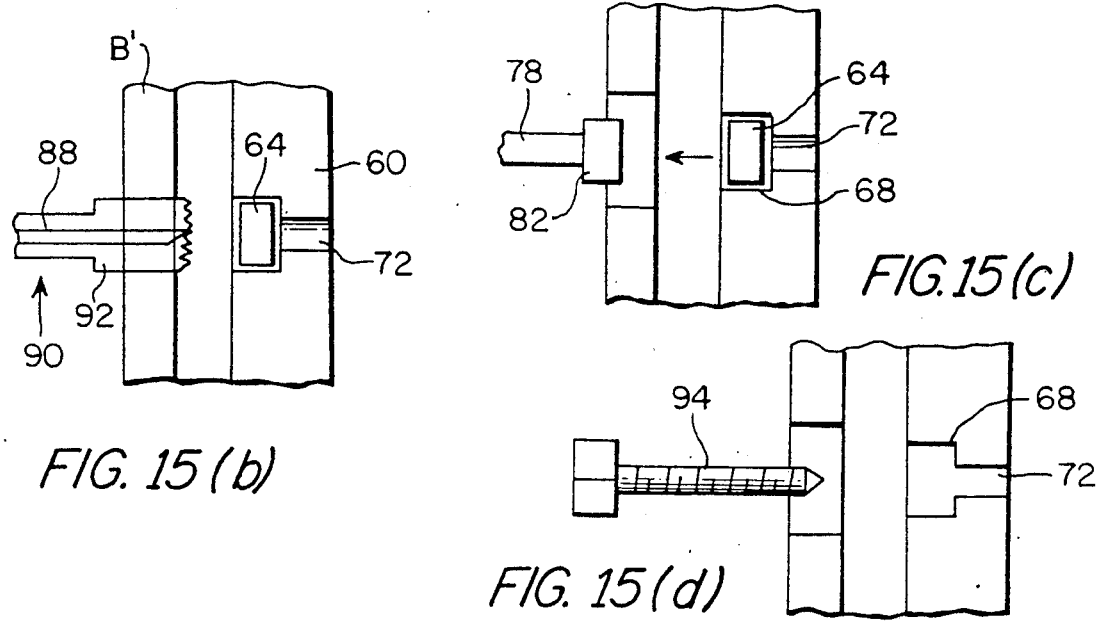

5,049,151

MAGNETIC POSITIONER ARRANGEMENT FOR LOCKING SCREWS FOR ORTHOPEDIC HARDWARD

FIELD OF THE INVENTION

The present invention relates to devices and arrangement for positioning locking screws or pins for orthopedic hardware such as interlocking rods and more particularly, to a locking screw or pin positioner for such hardware which employs cooperating magnets to enable precise positioning of such screws or pins.

BACKGROUND OF THE INVENTION

Orthopedic hardware that is inserted in an intramedullary manner has become an increasingly useful aid in treating complex fractures of long bones, e.g., of the femur or the tibia. In a typical application, an interlocking rod or bar, commonly referred to as a "nail," is inserted into a femur and transverse screws or pins, which are screwed or otherwise inserted from the outside of the limb or other body part through the bone and into distal and proximal transverse screw holes in the rod, are used to fix the rod in place in the bone.

The use of such locking screws to ensure that the rod is fixed firmly in position has extended the range of application of such orthopedic aids and appliances well beyond than that of the original locking rods without such transverse screws. However, the problem of properly inserting the screws from the outside of the limb is a difficult one and a number of different approaches have been taken in attempt to find a safe, effective and rapid way of inserting the locking screws and, in particular, the distal locking screws. In this regard, it is noted that such locking rods are long enough that the rods will bend when installed and thus locking or positioning devices which are centered based on a reference taken from the top of the rod have been ineffective in precisely locating the transverse screw holes. It will be understood that the locking screws or pins must be precisely located so that the load on the limb or other part of the body involved is transmitted through the screws or pins and associated interlocking rod and not through the broken portions of the bone during healing.

One method that is capable of providing precise locating of the holes distally uses x-ray techniques but long periods of x-ray exposure are required and the need to move the x-ray equipment in and out of position to check the screw or pin locations means that there is a risk of a loss of alignment each time the equipment is moved. As a consequence, the positioning of such locking screws or pins is typically the most time consuming and difficult portion of the overall rod implantation procedure.

Patents of interest in this field include Brudermann U.S. Pat. No. 4,621,628; Olerud et. al. U.S. Pat. No. 4,625,718, and Wu U.S. Pat. No. 4,570,624. The Brudermann patent discloses an apparatus for locating transverse holes in intramedullary implants and, in particular, transverse holes in the distal end of implanted locking "nails". The apparatus includes at least one magnet which generates an axially symmetrical field in combination with a magnetic field detecting device or sensor having an axial field reception characteristic. In one embodiment, the magnetic field sensor is inserted into an implanted nail and the magnet, which is placed on the surface of the skin, is moved until axes of the magnetic field of the magnet and the sensor are aligned. More particularly, the sensor is connected to an external display device and alignment of the respective magnetic fields is indicated when a zero-point indication is provided on the display device. A second magnet can be used to increase the precision of the alignment process.

The other two patents are thought to be of more general interest, with the Olerud et al patent disclosing an aiming apparatus using X-ray techniques for making holes or bores in the bone of patient in registration with the holes or bores on an interlocking nail, and the Wu patent disclosing a mechanical technique for aligning surgical pins in parallel.

SUMMARY OF THE INVENTION

In accordance with the invention, a method and apparatus are provided for positioning screws or pins of orthopedic hardware devices such as intramedullary rods, i.e., interlocking "nails," which overcome the problems of the prior art and enable rapid, efficient positioning and alignment of such screws or pins. Broadly speaking, the invention involves the positioning of a first magnet at the location of a screw hole in the nail and then using an aiming device, comprising a second magnet which interacts with the first magnet, to locate the first magnet and hence enable a screw or pin to be placed in the screw hole in the nail to lock the nail in position. As described in more detail below, in a first embodiment, an insertion rod is used to position the first magnet at the level of the hole in the rod while in a second embodiment, a solid nail is used and the magnet is removably disposed within the hole in the nail prior to implantation of the nail.

In contrast to the Brudermann patent discussed hereinabove, the magnetic field sensor or detector and thus, the expensive auxiliary equipment (e.g., the display, signal processing unit and connecting circuitry) associated with the sensor used in the Brudermann apparatus, are not required by the method and apparatus of the present invention. Moreover, no electrical circuits need be connected to the patient. In this latter regard, as noted above, the system of the Brudermann patents requires, in the illustrated embodiment, that an electrically powered device (the magnetic field detector) and associated electrical connecting wires, be positioned or placed within the intramedullary rod. It will be appreciated that any device which is electrically powered must be electrically isolated from the patient so as to prevent shock. Moreover, a magnetic field (flux) detector is a relatively delicate instrument that could be damaged during insertion and positioning within the interlocking rod. Moreover, cost of the system of the Brudermann patent and the training and skill required in the use of the instrumentation provided with that system are further disadvantages, particularly as compared with the system of the present invention.

In accordance with a first aspect of the invention, a positioning arrangement is provided for positioning locking screws or pins relative to screw holes in an orthopedic implant in the limb of a patient, the arrangement including a first magnet positioned in alignment with a said hole in the orthopedic implant so as to provide a directional magnetic field, and positioning means, including a further, pivotable magnet mounted for rotation about a pivot axis and also providing a directional magnetic field, for enabling the magnetic field of the further magnet to align with the magnetic field of the first magnet and thus provide alignment of the further magnet with the screw hole in the orthopedic implant at which the first magnet is positioned, thereby determining the path along which a locking screw or pin is to be advanced in order to engage in the screw hole in the implant.

The orthopedic implant preferably comprises an interlocking rod or "nail" implanted within a bone of a patient and including therein at least one said screw hole located at the distal end thereof, and according to the first embodiment of the invention referred to above, the interlocking rod is hollow, i.e., includes a longitudinal bore therein, as is the case with many conventional interlocking rods. In this embodiment, the positioning arrangement further comprises an elongate magnet carrying member at one end of which the first magnet is mounted and which is inserted into the interlocking rod to a depth corresponding to the location of the screw hole so as to center the magnet at that screw hole. The magnet carrying member advantageously comprises a non-magnetic insert (made, e.g., of plastic) at the one end in which the first magnet is mounted, with the insert having an outside diameter slightly less than the inside diameter of the bore in the interlocking rod. The magnet preferably comprises a cylindrical magnet disposed transversely to the longitudinal axis of said insert, and the insert is of a transverse cross-sectional shape such as to maintain the rotational orientation of the first magnet within the bore in the interlocking rod, i.e., such as to prevent rotation of the magnet within the rod. The further magnet also preferably includes a central axial bore therein for permitting the passage of a guide wire therethrough.

In a preferred embodiment, the positioning means comprises a universal joint and a bar member mounted by the universal joint, the further magnet being located at one end of the bar member and a counterbalancing weight being located at the other end of the bar member. The bar member, and the weight and the further magnet located thereon, include a longitudinal bore therethrough through which a guide wire can be passed so as to penetrate the bone in which the interlocking rod is implanted and enter into a screw hole in the interlocking rod in alignment with the further magnet.

In a further preferred embodiment, the positioning means includes a mounting case including opposed openings in the end walls thereof through which a guide wire can pass. Such a mounting case is advantageously provided with a relatively small sized version of the positioning means although its use is not limited to such an application.

In accordance with the second embodiment of the invention referred to above, the orthopedic implant comprises a solid rod and the first magnet is removably mounted in the screw hole in the rod. In this embodiment, a meltable substance, e.g., bone wax, having melting temperature such that the substance melts at the normal body temperature of a patient retains the first magnet in the screw hole.

In accordance with a further, related aspect of the overall invention, a method is provided for inserting a locking screw or pin into a screw or pin hole in an orthopedic aid implanted in a bone of a patient, the method comprising: disposing a first magnet within the bone at the location of the screw hole in the orthopedic aid within the bone; bringing a further, pivotally mounted magnet disposed externally of the patient close to the location of said first magnet so that the magnetic fields of the magnets interact and the axis of said further magnet aligns with the axis of said first magnet; inserting a locking screw or pin through the bone into the screw hole based on the alignment orientation of the further magnet.

In a preferred embodiment, a guide wire is inserted into the patient along the aligned axes of the magnets and the locking screw or pin is inserted over the guide wire into the screw hole in the orthopedic aid. Preferably, the further magnet includes a central opening therein and the guide wire is inserted through that opening.

The further magnet is advantageously mounted on a gimbal mount as mentioned above and the further magnet is permitted to move universally on that gimbal mount in order to align with that first magnet.

As was also discussed above, in a particularly useful application, the orthopedic aid comprises an interlocking rod including a plurality of said screw holes in the distal end thereof, and according to a further aspect of the invention, the method of the invention is repeated so as to insert locking screws into at least two such holes.

In one embodiment wherein the orthopedic aid comprises an interlocking rod, the further magnet is mounted on an elongate magnet carrier member as discussed above, and the magnet carrier is inserted down a central bore in the interlocking rod to the level of the screw hole into which a locking screw is to be inserted. As was also discussed above, the first magnet preferably comprises a cylindrical magnet disposed within a non-magnetic (e.g., "Teflon") insert carried by said carrier member and extends transversely to the longitudinal axis of the interlocking rod, and in accordance with the method of this embodiment, when the carrier member is inserted into the bore in the interlocking rod, the cylindrical first magnet is caused to align with the screw hole in the interlocking rod into which a locking screw is to be inserted.

Further, the carrier member preferably includes graduations along at least a portion of the length thereof corresponding to the depth of penetration of the carrier member into the bore in the interlocking rod, and the method further comprises using at least one of those graduations to ensure that the first magnet is disposed at a depth within the bore in the interlocking rod at which the first magnet is in alignment with the screw hole in the rod into which a locking screw is to be inserted.

In this overall embodiment, the first magnet is removed from a position at the location of the screw hole just prior to penetration by the wire through the bone to a position that permits the wire to be inserted into the screw hole in the orthopedic aid. In a specific version of this embodiment, the wire is made to penetrate through the first cortex of the bone and penetration is terminated just after the wire penetrates the second cortex of the bone. Preferably, a drill mounted on the wire is used to drill through the bone and adjacent soft tissue. Advantageously, the drill is removed from the guide wire after drilling, a depth gauge mounted on the guide wire is pressed down through the adjacent soft tissue to the outer edge of the first cortex of the bone to determine the depth of the wire in the bone, and a locking screw of a length corresponding to that depth is inserted over the guide wire to lock the orthopedic aid in place.

As noted above, in one embodiment of the positioning means of the invention, the further magnet is housed within a housing having aligned apertures in the end wall thereof; in aligning the further magnet of this embodiment, one of these end walls is preferably pressed against the soft tissue adjacent to the area of the bone in which is located the screw hole into which the locking screw is to be inserted.

As was also indicated above, the orthopedic aid can comprise a solid rod and in this embodiment, the first magnet is disposed and retained in a said screw hole in the solid rod in such a manner (e.g., through the use of bone wax) as to permit removal thereof prior to the insertion of a screw into that screw hole.

Other features and advantages of the invention will be set forth in, or apparent from, the following detailed description of preferred embodiments of the invention.

BRIEF DESCRIPTION OF THE DRAWINGS

FIG. 1 is a side elevational view, partially in section of a bone incorporating a screw positioning arrangement in accordance with a first preferred embodiment of the invention;

FIG. 2 is a rear end view of the aiming device of the arrangement of FIG. 1;

FIG. 3 is a side elevational view of the device of FIG. 2;

FIG. 11 is a side elevational view, similar to FIG. 1, showing a second embodiment of the positioning arrangement of the invention;

FIG. 14 is a side elevational view of a further embodiment of the aiming device of the invention in combination with a cross section of a portion of the interlocking rod of FIG. 11; and FIGS. 15(a) to 15(d) are schematic side elevational views of the steps employed in insertion of a screw, in a distal screw hole in the interlocking rod of the embodiment of FIG. 11.

DESCRIPTION OF THE PREFERRED EMBODIMENTS

Figure 4:
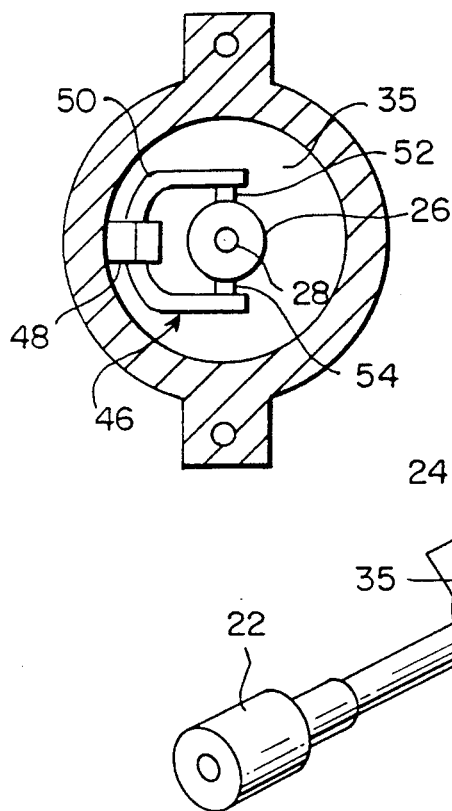
FIG. 4 is a cross sectional view of the device of FIG. 2 taken generally along line IV—IV of FIG. 3.
Figure 5:
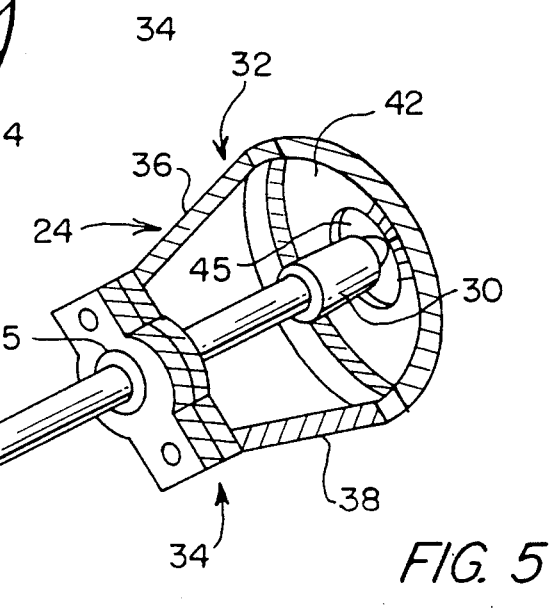
FIG. 5 is a front perspective view of the device of FIG. 2.

Referring to FIG. 1, there is shown a first embodiment of the positioning arrangement in accordance with the invention. As illustrated, an orthopedic "nail" 10 is implanted longitudinally within the intramedullary canal of a bone B (e.g. a femur). Nail 10, which is conventional and is described in more detail below, includes a longitudinal bore 12 therein as well as a pair of transversely extending, axially spaced screw holes or openings 14 and 16 at the distal end thereof. A carrier member or rod 18, which is also described in more detail below, is inserted into the bore 12 of nail 10 and carries a first magnet 20 at the distal end thereof. As described in more detail hereinafter, magnet 20 is mounted in a magnet carrier or mount 21 which is made of non-magnetic material (e.g., plastic) and is shaped to conform to the internal shape of the nail 10. As mentioned above and as set forth in more detail hereinbelow, a second magnet 22, mounted in an "aiming" device (more particularly, a gimbal device) denoted 24, is used in cooperation with magnet 20 to determine the positions of the holes 14 and 16 and thus permit locking screws or pins to be inserted in these holes to lock implant 10 in place within bone B. With this background or overview, the individual components of the positioning arrangement will now be considered.

Considering the aiming or gimbal device 24 in more detail, and referring particularly to FIGS. 2 to 5, as illustrated, gimbal device 24 includes a rod member 26 having a bore 28 therein through which a guide wire (not shown in FIGS. 2 to 5) is inserted. Magnet 22 is mounted at one of rod member 26 while a counterweight or counterbalancing element 30 is mounted on the other end thereof. Gimbal mount 24 further includes a cage or support assembly 32 comprising a central rod mounting section 34 having a central opening 35 therein, a pair of support arms 36, 38, and a rear ring section or ring 40 attached by support arms 36, 38 to rod mounting section 34. A clear plastic plate or face 42, containing graduations 44 thereon and having a central opening 44 therein, is secured to ring 40.

As illustrated in FIG. 4, rod member 26 is mounted for universal movement by a conventional gimbal mounting arrangement, generally denoted 46, including a stub shaft 48 affixed to the wall of rod mounting section 34 which defines opening 35, a U-shaped member 50 mounted for rotation on shaft 48 and a pair of pins 52, 54 which are pivotably mounted in the respective free ends of U-shaped member 50 and which are affixed to rod member 26 so as to enable rotation thereof about the axis defined by pins 52, 54. It will be understood that the gimbal mounting assembly depicted in FIG. 4 is conventional and that any universal mounting that would enable universal movement of rod member 26, and thus of magnet 22, can be employed.

It is noted that counterbalancing of the magnet 22 and, in particular, the provision of counterweight 30, is an important feature in that it enables aiming device 24 to be used without regard to the effect of gravity and thus permits interaction between magnets 22 and 20 irrespective of the position of the patient, i.e., whether the patient is laying on a side or is prone.

Figure 6A:
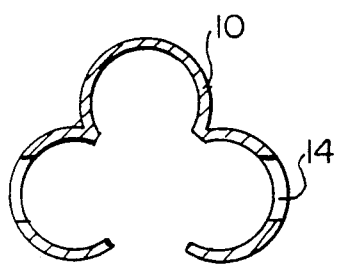
FIGS. 6(a) and 6(b) are, respectively, a cross sectional view and a partial side elevational view, respectively, of one form of interlocking rod.
Figure 6B:
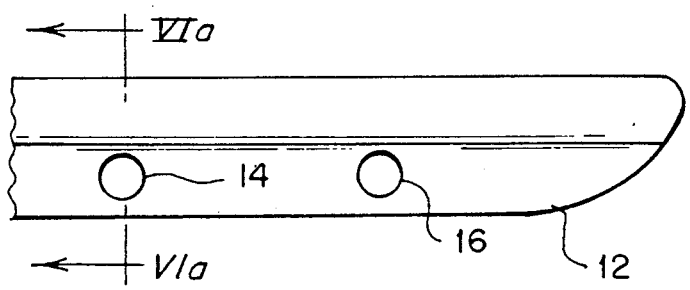
Figure 7A:
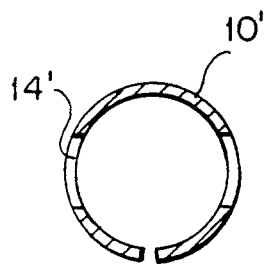
FIGS. 7(a) and 7(b) are, respectively, a cross sectional view and a partial side elevational view of a second form of interlocking rod.
Figure 7B:
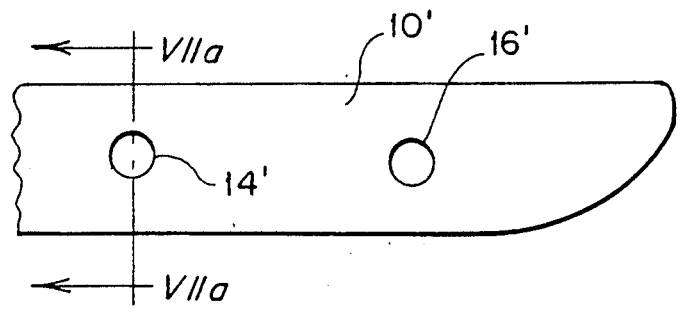

Referring to FIGS. 6(a) and 6(b) and FIGS. 7(a) and 7(b), two different forms of the nail or interlocking rod 10 of FIG. 1 are shown. In the embodiment of FIGS. 6(a) and 6(b), the nail 10 is in the general shape of a cloverleaf or a figure eight and includes a longitudinal split or opening at the bottom as shown, with screw holes 14 and 16 being provided in the bottom section or portion of the nail. In the embodiment of FIGS. 7(a) and 7(b), the nail, which is denoted 101, is circular in cross section and also includes screw holes 14' and 16' as well as a longitudinal split at the bottom thereof. It is to be understood that the nails shown in these figures are common forms of conventional intramedullary nails, and that the longitudinal splits at the bottoms (inferior sides) of the nails of both embodiments allows the nail to spring against the bone once the nail is in place.

Figure 8A:
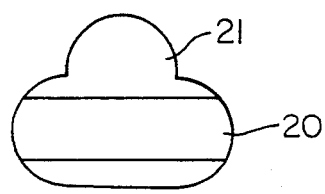
FIGS. 8(a) and 8(b) are, respectively, a cross sectional view and a side elevational view of a magnet insert or carrier adapted to be used with the rod of FIGS. 6(a) and 6(b)
Figure 9A:
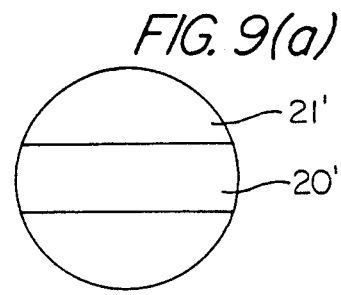
FIGS. 9(a) and 9(b) are, respectively, a cross sectional view and a side elevational view of a magnet insert or carrier adapted to be used with the rod of FIGS. 7(a) and 7(b)
Figure 8B:
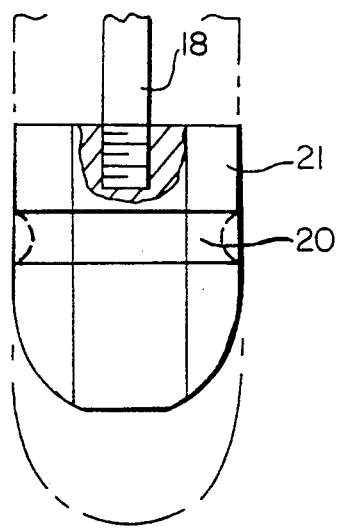
Figure 9B:
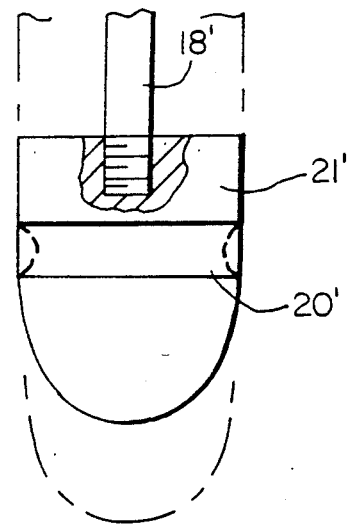

It might be helpful to note at this point that the preferred embodiment of the invention now being considered involves the provision of a positioning arrangement that can be used with any commercial nail, with the arrangement being tailored to a particular commercial nail. In this regard, as shown in FIGS. 8(a) and 8(b), magnet 20 and magnet holder or carrier 21 are shaped to match or conform to the internal shape of the clover leaf shaped nail 10 of FIGS. 6(a) and 6(b), while in FIG. 9(a) and 9(b), the magnet 20' and holder 21' are circular in shape to match the internal circular shape of nail 10' of FIGS. 7(a) and 7(b). In an exemplary embodiment, the holders 21 and 21' are 1 mm smaller in cross section than the corresponding nails 10 and 10'. The magnet holders 21 or 21' are preferably fabricated of "Teflon" or plastic and include internally threaded holes at the top in which the insertion rods 18 or 18' are received, as is indicated in FIGS. 8(b) and 9(b).

Figure 10:
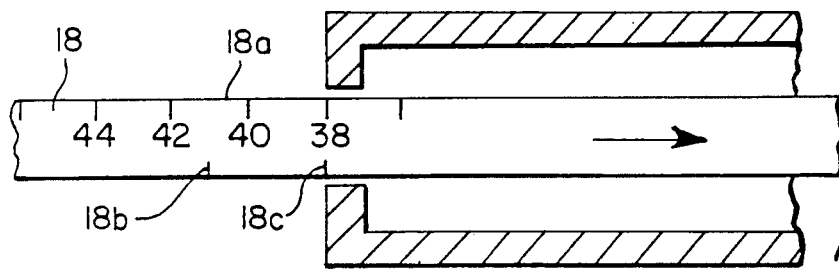
FIG. 10 is a side elevational view, partially broken away, of a detail of the insertion member of FIG. 1.

Referring to FIG. 10, a detail of insertion rod 18 is shown. As illustrated, insertion rod 18 includes a flattened portion that is provided with two sets of calibrations, one set comprising markings denoted 18a and the other comprising a pair of depth marks 18b and 18c. The set of markings that is denoted 18a comprises a series of conventional ruler markings (e.g., in centimeters or inches) which extend along one edge of rod 18 so as to provide a measurement in, e.g., centimeters, of the depth of the penetration of the rod 18 into the nail 10. The other set of markings, those denoted 18b and 18c, respectively correspond to the depth of penetration of the rod 18 into nail 10 at which the magnet 20 is in registration with screw hole 14 or with screw hole 16. In particular, in the example under consideration, marking 18b corresponds to the depth of the distal screw hole 16 while marking 18c corresponds to the depth of screw hole 14. It will, of course be understood that although most nails have only one or two screw holes at the distal end, the aiming or positioning system of the invention could be adapted to provide exact and rapid location of any number of holes at any location along a nail and could be used with a new generation of nails with multiple holes at multiple levels.

Before considering a further embodiment of the invention, the operation of the embodiment described above will be briefly considered in connection with FIG. 1. It is noted that a somewhat more complete description of the overall operation is provided below in connection with the second embodiment. As illustrated in FIG. 1, the insertion rod 18 has been inserted to a depth (indicated by marking 18b of FIG. 10) at which magnet 20 is in full alignment or registration with distal screw hole 16. In order to locate screw hole 16 from the outside of the limb in which bone B is located, the aiming device 24 shown in FIGS. 1 to 5 is brought into proximity to the general location of the screw hole 16. The device 24 preferably includes a protective case or cups as described below which is placed against the skin and pressed towards the intramedullary rod 10. In any event, the magnet 22 is free to move universally and the device moved around in this area until there is interaction between the magnetic files of magnets 20 and 22. Magnet 22 and counterweight 30 on shaft 26 will then align with the magnet 20 and a wire (not shown) can be drilled straight through the central bore 28 in shaft 26 (and through the tissue adjacent bone B) into the bone B. More particularly, a Kirschner rod or K-wire is drilled through the first cortex of bone B and stopped just after penetrating the second cortex of the bone. The magnet 20 is withdrawn (raised upwardly within bore 12 of nail 10) just prior to the final steps so that the drill (not shown) can pass through the screw hole 16. Once the drill hole is drilled into the bone B, the drill is removed from the K-wire and a depth gauge (not shown) is pressed down through the adjacent skin to the outer edge of the first cortex. The penetration of the K-wire in the bone is read by substraction. Next, a cannulated pin or screw (not shown) of the appropriate size and length (as determined by the depth gauge) is inserted over the K-wire into the screw hole 16 so as to lock nail 10 in place in the bone B. It will be appreciated that the locking screw or pin can be secured in place in the screw hole 16 by hand or using a power drill. The insertion rod 18 is then withdrawn to the second level, i.e., the level of screw hole 14, and a further screw or pin inserted into that hole in the same manner.

Figure 12:
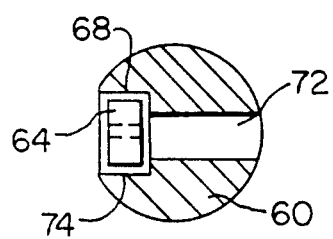
FIGS. 12 and 13 are a cross sectional view and a partial side elevational view, respectively, of the interlocking rod of FIG. 11 showing the magnet retained in a screw hole therein.
Figure 13:
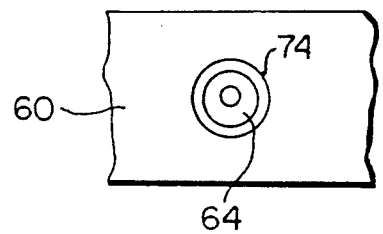

Referring now to FIGS. 11 to 13, a further embodiment of the invention is shown wherein the implanted nail, denoted 60 in FIG. 11, is a solid rod member. In this embodiment, magnets 62 and 64 are disposed in enlarged recesses 66 and 68 in respective screw holes 70 and 72 prior to implantation of nail 60. In a preferred embodiment, magnets 62 and 64 are releasably retained in place in respective recesses 66 and 68 by a substance, such as bone wax, indicated at 74, which melts at body temperature (98.6° F.) so that the magnets can be removed.

An aiming device 24' is shown in FIG. 11, corresponding to aiming device 24 of FIG. 1, although it will be understood that other versions or implementations of the aiming device can be employed with both embodiments. In this regard, referring to FIG. 14, a simplified, miniaturized aiming device 76 is shown which includes a relatively short, hollow bar 78 mounted on a conventional gimbal mount indicated at 80 and including a magnet 82 at one end and a counterweight 84 at the other end. The aiming device 76 further includes an outer sterile plastic case or housing 86, meaning so that the aiming device 76 is encapsulated within a small sterile package.

This embodiment is easy to handle and is small enough to be able to be placed down against a bone, e.g., through a small skin opening, in order to minimize the distance between the magnet 82 and the magnet 64 within the implant. This embodiment also facilitates insertion of screws into an implant in a tight space A further application of this embodiment involves situations where the bone is exposed, as where there is a large open injury and associated destruction of the protective soft tissue. In such a situation, the fracture fragments of the bone can be locked to the interlocking rod at several different levels using the aiming device 76 of FIG. 14. In this regard, in such a situation, the device 76 can be placed directly against the bone, thereby ensuring accurate placement of the screws by minimizing the distance between the coupling magnets. Further, although as described below, the case or housing 86 includes holes in the end walls to permit a drill wire to be inserted therethrough, the case or housing 86 can also be designed so as to be slipped back as indicated in dashed lines in FIG. 14 so that the magnet 82 can, e.g., be brought into direct contact with an exposed bone.

Referring to FIGS. 15(a) to 15(d), the steps used in implanting a locking screw are shown, i.e., the steps which are followed subsequently to the magnet 82 being caused to align with magnet 64 (as illustrated in FIG. 14). Once the magnet 64 is localized as shown in FIG. 14, a small (thin) guide pin or wire 88 is inserted (e.g., down the bore in bar or shaft 78) through the limb and the bone B' to a position near to magnet 64 as illustrated in FIG. 15(a). Thereafter, a small reamer 90, having a reaming head 92 larger than magnet 64, is inserted over pin 89 to cut out a core piece of the bone B', in line with the guide hole provided by the pin, as illustrated in FIG. 15(b), so as to leave an opening or hole therein. A magnet, (e.g., magnet 82 of the aiming device 76 of FIG. 14) is then advanced to a position wherein the magnetic force generated thereby serves to pull the magnet 64 out of recess 68 as illustrated in FIG. 15(c). In a specific exemplary embodiment, a force of at least 3.5 pounds for the distance illustrated is necessary to remove the magnet 64. It will be appreciated that magnet 64 would at this time be loosely held in recess or hole 68 by the melted bone wax. With magnet 64 removed, a path is opened for the insertion of screw 94 into screw hole 72, as illustrated in FIG. 15(d). This procedure is, of course, repeated in removing magnet 62 and in inserting a screw into screw hole 70.

It is noted that for normal use, i.e., in situations where the second magnet cannot be placed directly against the bone, very strong magnets are required in order to provide the necessary interaction and resultant alignment of the magnets. In this regard, it has been found that magnets providing a flux density of at least about 27 to 35 million Oersteds should be used. A preferred magnet is made of Neodymium-Iron-Boron.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A positioning arrangement for positioning locking screws or pine relative to screw holes in an orthopedic implant in the limb of a patient, said arrangement including a first permanent magnet positioned in alignment with a said hole in a said orthopedic implant and providing a directional magnetic field, a further permanent magnet providing a directional magnetic field, and positioning means, including means defining a pivot axis, for mounting said further magnet so as to freely pivot about said pivot axis so as to enable the magnetic field of said further magnet to align with the magnetic field of the first magnet and thus provide alignment of the further magnet with the screw hole in the orthopedic implant at which said first magnet is positioned, thereby determining the path along which a locking screw or pin is to be advanced in order to engage in said screw hole in the implant.

2. An arrangement as claimed in claim 1 wherein said orthopedic implant comprises an interlocking rod, having distal and proximal ends, implanted within a bone of a patient and including therein at least one said screw hole located at the distal end thereof, said interlocking rod including a longitudinal bore therein and said arrangement further comprising an elongate magnet carrying member at one end of which said first magnet is mounted and which is inserted into said rod to a depth corresponding to the location of the screw hole so as to center the magnet at said screw hole.

3. An arrangement as claimed in claim 2 wherein said magnet carrying member comprises a non-magnetic insert at said one end in which said first magnet is mounted, said insert having an outside diameter slightly less than the inside diameter of said bore in said interlocking rod.

4. An arrangement as claimed in claim 3 wherein said magnet carrying member includes graduations along at least a portion of the length thereof for assisting in determining the depth to which said member is to be inserted into the interlocking rod to bring said further magnet into alignment with a selected screw hole.

5. An arrangement as claimed in claim 3 wherein said first magnet comprises a cylindrical magnet disposed transversely to the longitudinal axis of said insert, and wherein said insert is of a transverse cross-sectional shape relative to the transverse cross-sectional shape of the bore of the locking rod such as to prevent rotation of said first magnet within the bore in said interlocking rod.

6. An arrangement as claimed in claim 1 wherein said further magnet includes a central axial bore therein for permitting the passage of a guide wire therethrough.

7. An arrangement as claimed in claim 1 wherein said positioning means comprises a universal joint and a bar member mounted by said universal joint, said further magnet being located at one end of said bar member and a counterbalancing weight being located at the other end of said bar member.

8. An arrangement as claimed in claim 7 wherein said bar member, and said weight and said further magnet located thereon, include a longitudinal bore therethrough through which a guide wire can be passed so as to penetrate the bone in which the interlocking rod is implanted and enter into a screw hole in the interlocking rod in alignment with said further magnet.

9. An arrangement as claimed in claim 1 wherein said positioning means includes a mounting case including opposed openings in the end walls thereof through which a said wire can pass.

10. An arrangement as claimed in claim 1 wherein said orthopedic implant comprises a solid rod and said first magnet is removably mounted in the screw hole in the rod.

11. An arrangement as claimed in claim 10 wherein a meltable substance having melting temperature such that the substance melts at the normal body temperature of a patient retains said first magnet in said screw hole.

12. A method for inserting a locking screw or pin into a screw hole in an orthopedic aid implanted in a bone of a patient, said method comprising
    disposing a first permanent magnet within the bone at the location of the screw hole in the orthopedic aid within the bone;
    bringing a further permanent magnet, mounted so as to freely pivot about a pivot axis of a positioning device, into a position externally of the patient close to the location of said first magnet so that the magnetic fields of the magnets interact to cause the further magnet to freely pivot about said pivot axis so that the axis of said further magnet aligns with the axis of said first magnet; and
    inserting a locking screw or pin through the bone into said screw hole based on the orientation of the further magnet when aligned with said first magnet.

13. A method as claimed in claim 12 further comprising inserting a guide wire into the patient along the aligned axes of the magnets; and inserting said locking screw over the wire into the screw hole in the orthopedic aid.

14. A method as claimed in claim 13 wherein said further magnet includes a central opening therein and said guide wire is inserted through said opening.

15. A method as claimed in claim 12 wherein said further magnet is mounted on a gimbal mount and said further magnet is permitted to move universally on said gimbal mount in order to align with said first magnet.

16. A method as claimed in claim 12 wherein said orthopedic aid comprises an interlocking rod having proximal and distal ends and including a plurality of said screw holes in the distal end thereof, and said method is repeated so as to insert locking screws into at least two of said holes.

17. A method a claimed in claim 14 wherein said orthopedic aid comprises an interlocking rod, said further magnet is mounted on an elongate magnet carrier member, and said magnet carrier is inserted down a central bore in said interlocking rod to the level of the screw hole into which a locking screw is to be inserted.

18. A method as claimed in claim 17 wherein said first magnet comprises a cylindrical magnet disposed within a non-magnetic insert carried by said carrier member and extends transversely to the longitudinal axis of the interlocking rod, and wherein when said carrier member is inserted into the bore in said interlocking rod, said cylindrical first magnet is caused to align with the screw hole in the interlocking rod into which a locking screw is to be inserted.

19. A method as claimed in claim 17 wherein said carrier member includes graduations along at least a portion of the length thereof corresponding to the depth of penetration of the carrier member into the bore in the interlocking rod and wherein said method further comprises using at least one of said graduations to ensure that said first magnet is disposed at a depth within the bore in the interlocking rod at which the first magnet is in alignment with the screw hole in the rod into which a locking screw is to be inserted.

20. A method as claimed in claim 13 wherein said first magnet is removed from a position at the location of said screw hole just prior to penetration by the wire through the bone to a position wherein the wire can be inserted into the screw hole in the orthopedic aid.

21. A method as claimed in claim 13 wherein the wire is made to penetrate through the first cortex of the bone and penetration is terminated just after the wire penetrates the second cortex of the bone.

22. A method as claimed in claim 13 wherein a drill mounted on said wire is used to drill through the bone and adjacent soft tissue.

23. A method as claimed in claim 22 wherein said drill is removed from said guide wire after drilling, a depth gauge mounted on said guide wire is pressed down through the adjacent soft tissue to the outer edge of the first cortex of said bone to determine the depth of the wire in the bone, and a locking screw of a length corresponding to said depth is inserted over the guide wire to lock the orthopedic aid in place.

24. A method as claimed in claim 23 wherein said further magnet is housed within a housing having aligned apertures in the end wall thereof and wherein, in aligning the further magnet, one of said end walls is pressed against the soft tissue adjacent to the area of the bone in which is located the screw hole into which said locking screw is to be inserted.

25. A method as claimed in claim 12 wherein said orthopedic aid comprises a solid rod and wherein said first magnet is disposed in a said screw hole in said solid rod in such a manner as to permit removal thereof prior to the insertion of a screw into said screw hole.

* * * * *